(12) United States Patent
Korpimaki (10) Patent No.: US 10,151,672 B2
(45) Date of Patent: Dec. 11, 2018

(54) DEVICE AND A METHOD FOR MANAGING A SAMPLE TO BE ANALYZED AND A SOLID SAMPLE CARRIER AND LIQUID SAMPLE CARRIER

(71) Applicant: WALLAC OY, Turku (FI)

(72) Inventor: Teemu Korpimaki, Turku (FI)

(73) Assignee: WALLAC OY, Turku (FI)

( * ) Notice: Subject to any disclaimer, the term of this patent is extended or adjusted under 35 U.S.C. 154(b) by 73 days.

(21) Appl. No.: 15/117,519

(22) PCT Filed: Feb. 2, 2015

(86) PCT No.: PCT/FI2015/050066
§ 371 (c)(1),
(2) Date: Aug. 9, 2016

(87) PCT Pub. No.: WO2015/121533
PCT Pub. Date: Aug. 20, 2015

(65) Prior Publication Data
US 2016/0356680 A1    Dec. 8, 2016

Related U.S. Application Data

(60) Provisional application No. 61/938,287, filed on Feb. 11, 2014.

(30) Foreign Application Priority Data

Feb. 11, 2014   (FI) ..................................... 20145132

(51) Int. Cl.
*G01N 1/28* (2006.01)
*G01N 21/03* (2006.01)
(Continued)

(52) U.S. Cl.
CPC .............. *G01N 1/286* (2013.01); *B01L 3/508* (2013.01); *G01N 21/03* (2013.01); *G01N 21/63* (2013.01);
(Continued)

(58) Field of Classification Search
None
See application file for complete search history.

(56) References Cited

U.S. PATENT DOCUMENTS 4,234,378 A    11/1980    Iwasaki et al.
6,649,403 B1   11/2003    McDevitt et al.
(Continued)

FOREIGN PATENT DOCUMENTS

WO    2004/008146 A2    1/2004
WO    2008/014223 A2    1/2008
(Continued)

OTHER PUBLICATIONS

International Search Report, dated May 18, 2015, from corresponding PCT application.
(Continued)

*Primary Examiner* — Kathryn Wright
(74) *Attorney, Agent, or Firm* — Young & Thompson (57) ABSTRACT

A device for managing a sample to be analyzed comprises magnetizing equipment (302) for producing magnetic field capable of interacting, when the sample is moving to or located in a sample well, with magnetically amplifying material attached to the sample, where the magnetically amplifying material has relative magnetic permeability constant greater than one. With the aid of the magnetizing element the movement of the sample to the sample well and/or the position of the sample in the sample well can be monitored and/or controlled. The device can be, for example
(Continued)

but not necessarily, an instrument for dispensing samples to sample wells or an optical measurement instrument.

12 Claims, 4 Drawing Sheets

(51) Int. Cl.
- *G01N 21/63* (2006.01)
- *B01L 3/00* (2006.01)
- *G01N 35/00* (2006.01)
- *G01R 33/02* (2006.01)

(52) U.S. Cl.
CPC ......... *G01N 35/0098* (2013.01); *G01R 33/02* (2013.01); *B01L 2300/0887* (2013.01); *B01L 2300/12* (2013.01); *B01L 2300/126* (2013.01); *G01N 2001/288* (2013.01); *G01N 2001/2873* (2013.01)

(56) References Cited

U.S. PATENT DOCUMENTS

| | | |
|---|---|---|
| 2004/0101966 A1 | 5/2004 | Davis et al. |
| 2006/0210435 A1 | 9/2006 | Alavie et al. |
| 2012/0034703 A1 | 2/2012 | Nguyen et al. |

FOREIGN PATENT DOCUMENTS

| | | |
|---|---|---|
| WO | 2009/012372 A1 | 1/2009 |
| WO | 2009/065307 A2 | 5/2009 |
| WO | 2010/037907 A1 | 4/2010 |
| WO | 2013/019137 A1 | 2/2013 |
| WO | 2013/158044 A1 | 10/2013 |
| WO | 2013/179069 A1 | 12/2013 |

OTHER PUBLICATIONS

FI Search Report, dated Oct. 10, 2014, from corresponding FI application.

DEVICE AND A METHOD FOR MANAGING A SAMPLE TO BE ANALYZED AND A SOLID SAMPLE CARRIER AND LIQUID SAMPLE CARRIER

FIELD OF THE INVENTION

The invention relates to a method and a device for managing a sample to be examined. The device can be, for example but not necessarily, an instrument for dispensing samples to sample wells or an optical measurement instrument. Furthermore, the invention is related to a solid sample carrier suitable for collecting samples of biological material to be analyzed. Furthermore, the invention is related to liquid sample carrier suitable for carrying biological material to be analyzed.

BACKGROUND

One conventional practice is to impregnate one or more drops of fluid samples to be analyzed onto a solid sample carrier, dry the solid sample carrier impregnated with the fluid, and then send the solid sample carrier to a laboratory for analysis. The fluid to be analyzed can be, for example, blood of a newborn baby and the solid sample carrier can be, for example, a sheet of paper or some other suitable material which is able to carry the fluid to be analyzed. In the laboratory, one or more pieces containing the dried fluid to be analyzed are cut off from the solid sample carrier and the one or more pieces that have been cut off are conveyed, for further analysis, to one or more sample wells of e.g. a microtitration plate or some other sample well element. Each piece can be cut off from the solid sample carrier for example with a punch and a die provided with a channel for the punch, where the punch is arranged to cut off the piece with a single stroke through the solid sample carrier. It is also possible to use a cutting instrument capable of producing a localized, point-form cut on the solid sample carrier and to move the point-form cutting impact produced by the cutting instrument along the outer periphery of each piece so as to detach the piece from the solid sample carrier. Another conventional practice is to handle the sample to be analyzed in liquid form so that the sample is blended or dissolved in liquid sample carrier. In this case, one or more drops of the liquid sample carrier containing the sample are dispensed to one or more sample wells for further analysis.

One challenge related to the above-mentioned practices is the need to ensure that pieces cut off from a solid sample carrier containing sample or drops of liquid sample carrier containing sample are appropriately conveyed to right sample wells. Furthermore, when using pieces cut off from a solid sample carrier, it would be advantageous if the position of a piece in a sample well can be controlled when or after liquid that dissolves sample material or certain components of the sample material from the piece is or has been added to the sample well. For example, in conjunction with some optical measurements, it would be advantageous to ensure that the piece is located on the bottom of the sample well instead of floating on the surface of the liquid that has been added to the sample well.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In this document the term "solid" means that material under consideration is in none of the following phases: gas, plasma, and liquid.

In the context of this document, the term "solid" does not exclude porousness and other kind of ability to be impregnated with liquid. Therefore, in the context of this document, solid material can be porous or otherwise capable of being impregnated with liquid. Furthermore, the term "solid" does not exclude plasticity, elasticity, and flexibility of material under consideration. Yet furthermore, the term "solid" does not exclude mosaic structure of an object under consideration.

In this document, the term "solid sample carrier" means a carrier made of solid material, e.g. a sheet of paper, capable of carrying sample material and the term "liquid sample carrier" means carrier liquid i.e. liquid capable of carrying sample material.

In accordance with the invention, there is provided a new device for managing a sample to be analyzed. The device according to the invention comprises:

magnetizing equipment for producing magnetic field capable of interacting, when the sample is moving to or located in a sample well, with magnetically amplifying material attached to the sample, the magnetically amplifying material having relative magnetic permeability constant greater than one, i.e. $\mu_r > 1$.

With the aid of the magnetizing element the movement of the sample to the sample well and/or the position of the sample in the sample well can be monitored and/or changed. Thus, in this document, the verb "to manage" is to be understood in a broad sense so that it may mean, inter alia, mere checking actions for monitoring purposes, or control actions influencing an object under consideration, or both. The device can be, for example but not necessarily, an instrument for dispensing samples to sample wells or an optical measurement instrument.

In accordance with the invention, there is also provided a new method for managing a sample to be analyzed. The method according to the invention comprises:

producing magnetic field capable of interacting with magnetically amplifying material attached to the sample, and managing the sample with the aid of the magnetic field when the sample is moving to or located in a sample well.

In accordance with the invention, there is also provided a new solid sample carrier suitable for collecting samples of biological material to be analyzed. The solid sample carrier according to the invention comprises:

a body capable of carrying the biological material, and magnetically amplifying material combined with the body.

The body of the solid sample carrier can be, for example, a sheet of paper or some other suitable material which is able to carry the biological material to be analyzed.

In accordance with the invention, there is also provided new liquid sample carrier suitable for carrying biological material to be analyzed. The liquid sample carrier according to the invention is a colloid with dispersed phase particles comprising magnetically amplifying material having relative magnetic permeability constant greater than one. The particles are ferro- or paramagnetic and their sizes can be, for example, on micro- or nanometer-class. The particles can be, for example, poly-vinyl-alcohol "PVA" particles which contain magnetite. The diameter of the PVA particles can be, for example, about 1-2 μm.

A number of exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of unrecited features. The features recited in depending claims are mutually freely combinable unless otherwise explicitly stated.

BRIEF DESCRIPTION OF FIGURES

The exemplifying embodiments of the invention and their advantages are explained in greater detail below in the sense of examples and with reference to the accompanying drawings, in which.

DESCRIPTION OF EXEMPLIFYING EMBODIMENTS

Figure 1:
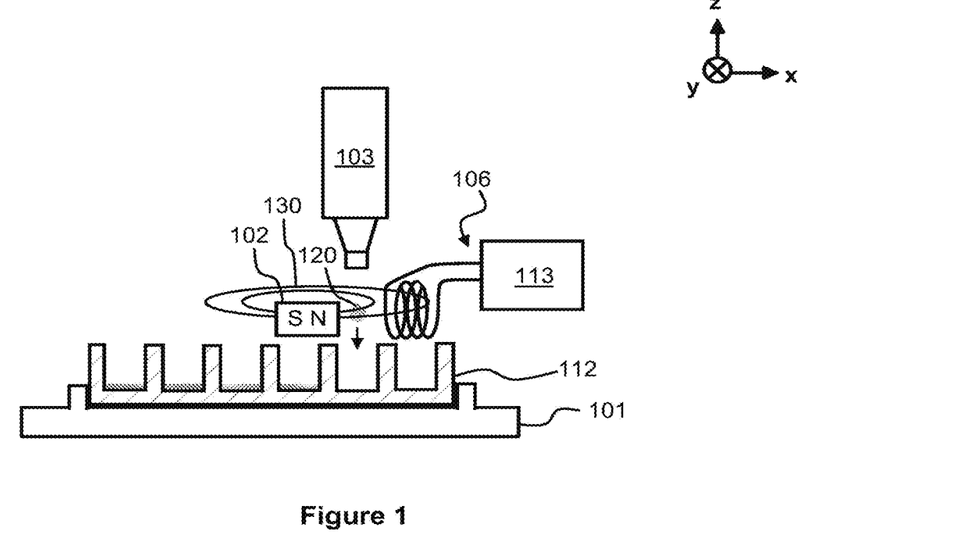
FIG. 1 shows a schematic side view of a device according to an exemplifying embodiment of the invention.

FIG. 1 shows a schematic side view of a device according to an exemplifying embodiment of the invention. In this exemplifying case, the device is an instrument for dispensing samples to sample wells. The device comprises a support element 101 for supporting a sample well element 112, e.g. a microtitration plate, comprising one or more sample wells. In FIG. 1, the sample well element 112 is presented as a section view. The device comprises a dispensing element 103 for dispensing a sample, and the support element 101 is configured to support the sample well element 112 so that an appropriate sample well is able to receive the sample from the dispensing element 103. In the exemplifying case illustrated in FIG. 1, the dispensing element 103 comprises a pipette for dispensing liquid sample carrier. The dispensed quantity 120 of the liquid sample carrier contains the sample to be analyzed. The liquid sample carrier is a colloid with dispersed phase particles comprising magnetically amplifying material that has relative magnetic permeability constant greater than one, i.e. $\mu_r > 1$. The particles can be, for example, polyvinyl-alcohol "PVA" particles containing magnetite. The PVA particles containing magnetite are colloidally stable and chemically inert. In FIG. 1, the dispensed quantity 120 of the liquid sample carrier containing the sample to be analyzed is presented as a drop.

The device comprises magnetizing equipment 102 for producing magnetic field 130 capable of interacting with the magnetically amplifying material attached to the sample. When the sample is moving from the dispensing element 103 to the sample well, the magnetically amplifying material attached to the sample causes a change in the magnetic field. The device further comprises a sensor 106 for detecting the change in the magnetic field so as to monitor whether the sample is correctly moved to the sample well. In the exemplifying case shown in FIG. 1, the magnetizing equipment 102 is a piece of permanent magnet material but it is also possible that the magnetizing equipment comprises a coil connected to a source of electrical current. The sensor 106 comprises a coil for producing a signal indicative of changes in the magnetic field and a processor 113 for processing the signal into a form suitable for further use.

Figure 2A:
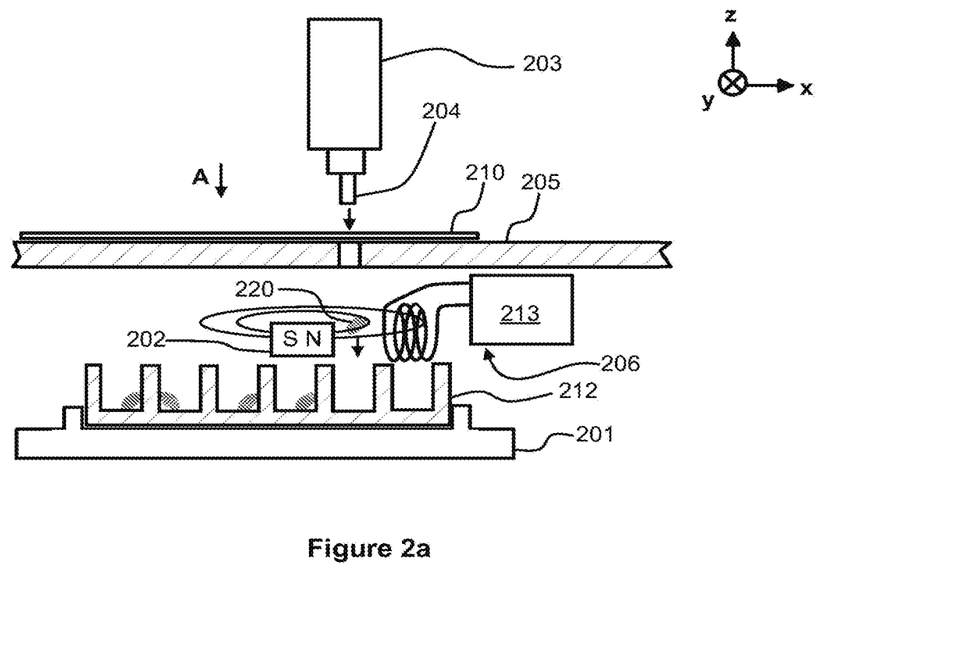
FIG. 2a shows a schematic side view of a device according to another exemplifying embodiment of the invention.

FIG. 2a shows a schematic side view of a device according to an exemplifying embodiment of the invention. The device is an instrument for dispensing samples to sample wells. The device comprises a support element 201 for supporting a sample well element 212 comprising sample wells. In FIG. 2a, the sample well element 212 is presented as a section view. It is to be noted that the sample well element 212 is not necessarily an integral part of the device because the sample well element is a replaceable component and devices of the kind described here can be delivered to laboratories etc. without sample well elements and the sample well elements can be delivered by different vendors. The device comprises a dispensing element 203 for dispensing a sample, and the support element 201 is configured to support the sample well element 212 so that an appropriate sample well is able to receive the sample from the dispensing element 203. In the exemplifying case illustrated in FIG. 2a, the dispensing element 203 comprises a cutting element for cutting off a piece from a solid sample carrier 210 that is a solid sample carrier according to an exemplifying embodiment of the invention. The solid sample carrier 210 is suitable for collecting samples of material to be analyzed, e.g. blood of a newborn baby. The cutting element comprises a punch 204 and a die 205 provided with a channel for the punch. The punch is arranged to cut off the piece from the solid sample carrier 210 with a stroke through the solid sample carrier. It is also possible that the cutting element comprises a cutting instrument for producing a point-form cut on the solid sample carrier and equipment for directing the cutting instrument so that cutting impact produced by the cutting instrument is moved along the outer periphery of the piece so as to cut off the piece. The above-mentioned cutting instrument can be, for example, a laser beam cutter or a liquid, e.g. water, jet cutter.

Figure 2B:
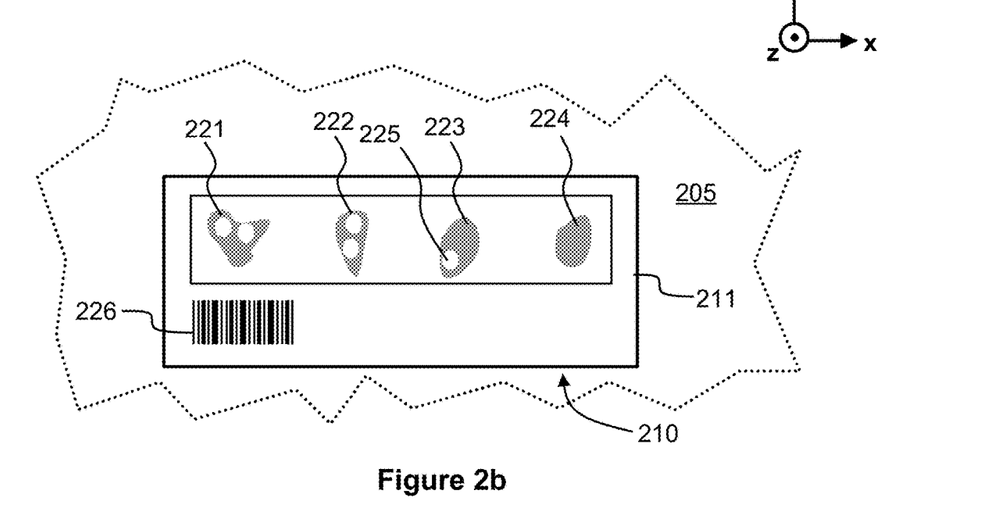
FIG. 2b shows a solid sample carrier according to an exemplifying embodiment of the invention.

FIG. 2b illustrates the solid sample carrier 210 by showing a view seen along the arrow B presented in FIG. 2a. The solid sample carrier comprises a body 211 capable of carrying the sample material to be analyzed. The body can be, for example, a sheet of paper or some other suitable, and preferably porous, material which is able to carry the sample material to be analyzed. Blotches 221, 222, 223 and 224, shown in FIG. 2b, on the solid sample carrier 210 are the regions of the solid sample carrier into which the sample material has been impregnated. Pieces are cut off from the regions of the solid sample carrier into which the sample material has been impregnated. For example, the piece 220 shown in FIG. 2a has been cut off from the region 223 shown in FIG. 2b. The region 223 has a hole 225 on the place from which the piece 220 has been cut off. After cutting, the detached piece 220 is conveyed, i.e. dropped in this case, for further analysis to a sample well of the sample well element 212 shown in FIG. 2a. The solid sample carrier 210 may comprise a machine-readable identifier 226 that may contain, for example, information about the donor of the sample material, information about the time and place of taking the sample, and/or other appropriate information.

The solid sample carrier 210 comprises magnetically amplifying material combined with the body 211. In a solid sample carrier according to an exemplifying embodiment of the invention, the body 211 is a sheet of paper that comprises magnetically amplifying particles, e.g. iron, magnetite, or ferrite particles, among fibers of the paper. The paper can be provided with the magnetically amplifying particles, for example, during manufacture of the paper. A solid sample carrier according to another exemplifying embodiment of the invention comprises, on the reverse surface of the body 211, a layer containing magnetically amplifying material. The layer can be, for example, a layer of magnetically amplifying paint or a layer of magnetically amplifying particles functionalized with e.g. isocyanate that is able to combine with cellulose covalently. A solid sample carrier according to an exemplifying embodiment of the invention comprises a layer of plastic between the body and the layer containing the magnetically amplifying material.

The device illustrated in FIG. 2a comprises magnetizing equipment 202 for producing magnetic field capable of interacting with the magnetically amplifying material attached to the piece 220. When the piece is moving from the dispensing element 203 to the sample well, the magnetically amplifying material attached to the piece causes a change in the magnetic field. The device further comprises a sensor 206 for detecting the change in the magnetic field so as to monitor whether the piece 220 is correctly moved to the sample well. The sensor 206 comprises a coil for producing a signal indicative of changes in the magnetic field and a processor 213 for processing the signal into a form suitable for further use.

Figure 3:
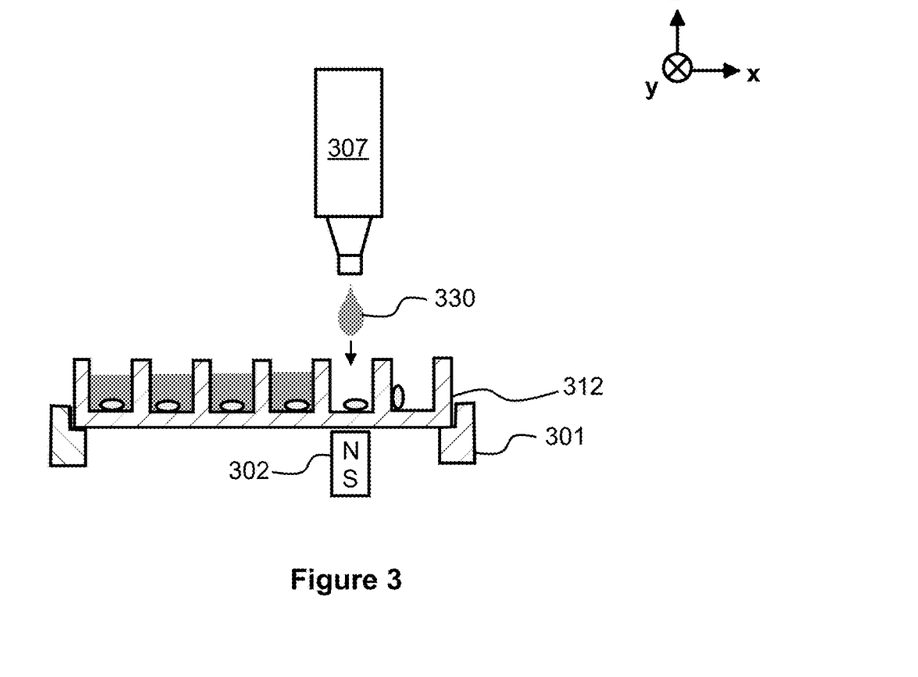
FIG. 3 shows a schematic side view of a device according to an exemplifying embodiment of the invention.

FIG. 3 shows a schematic side view of a device according to an exemplifying embodiment of the invention. The device comprises a support element 301 for supporting a sample well element 312 comprising sample wells. In FIG. 3, the sample well element 312 is presented as a section view. In the situation shown in FIG. 3, each sample well contains a piece that has been cut off from a solid sample carrier and that has been impregnated with sample material to be analyzed, e.g. blood. Furthermore, the piece contains magnetically amplifying material. The device is configured to add, to each sample well, liquid which dissolves the sample material or certain components of the sample material from the piece. The device comprises a liquid dispenser 307 for adding the liquid to each sample well. Furthermore, the device comprises magnetizing equipment 302 arranged to produce magnetic field on the vicinity of the bottom of an appropriate sample well so that the magnetic field is capable of drawing the piece to the bottom of the sample well when the liquid is added to the sample well. Thus, it can be ensured that the piece does not get floating on the surface of the liquid and that the piece is relevantly surrounded by the liquid.

Figure 4:
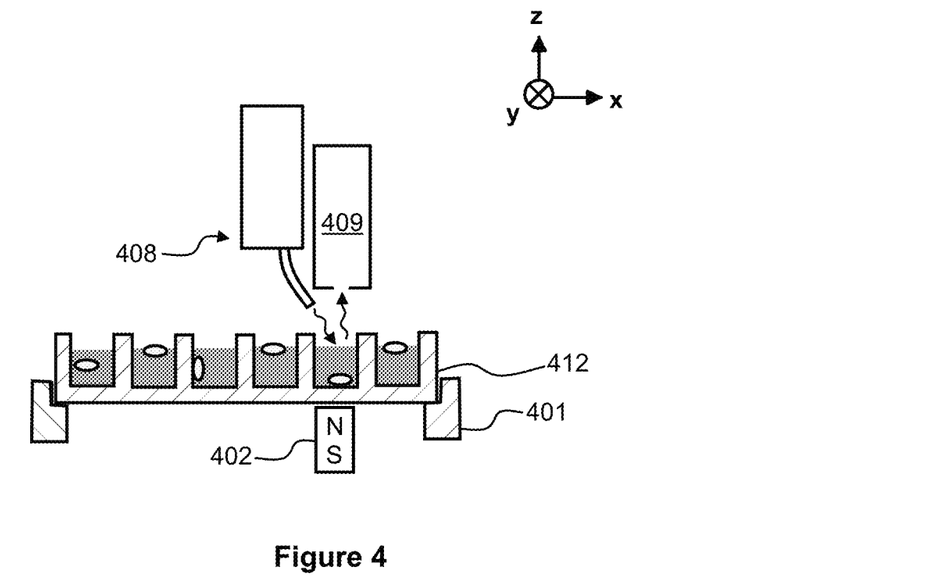
FIG. 4 shows a schematic side view of a device according to an exemplifying embodiment of the invention.

FIG. 4 shows a schematic side view of a device according to an exemplifying embodiment of the invention. In this exemplifying case, the device is an optical measurement instrument. The device comprises a support element 401 for supporting a sample well element 412, e.g. a microtitration plate, comprising sample wells. In FIG. 4, the sample well element 412 is presented as a section view. In the situation shown in FIG. 4, each sample well contains a piece that has been cut off from a solid sample carrier and that has been impregnated with sample material to be analyzed, e.g. blood. Furthermore, the piece contains magnetically amplifying material. In addition to the piece, each sample well contains liquid which has dissolved the sample material or certain components of the sample material from the piece. The device further comprises a light source 408 for directing excitation light to the liquid contained by a sample well and a detector 409 for measuring light emitted by the liquid contained by the sample well. The device comprises magnetizing equipment 402 arranged to produce magnetic field on the vicinity of the bottom of the sample well so that the magnetic field is capable of drawing the piece to the bottom of the sample well when the light emitted by the liquid contained by the sample well is measured. Thus, it can be ensured that the piece does not disturb the optical measurement.

Figure 5:
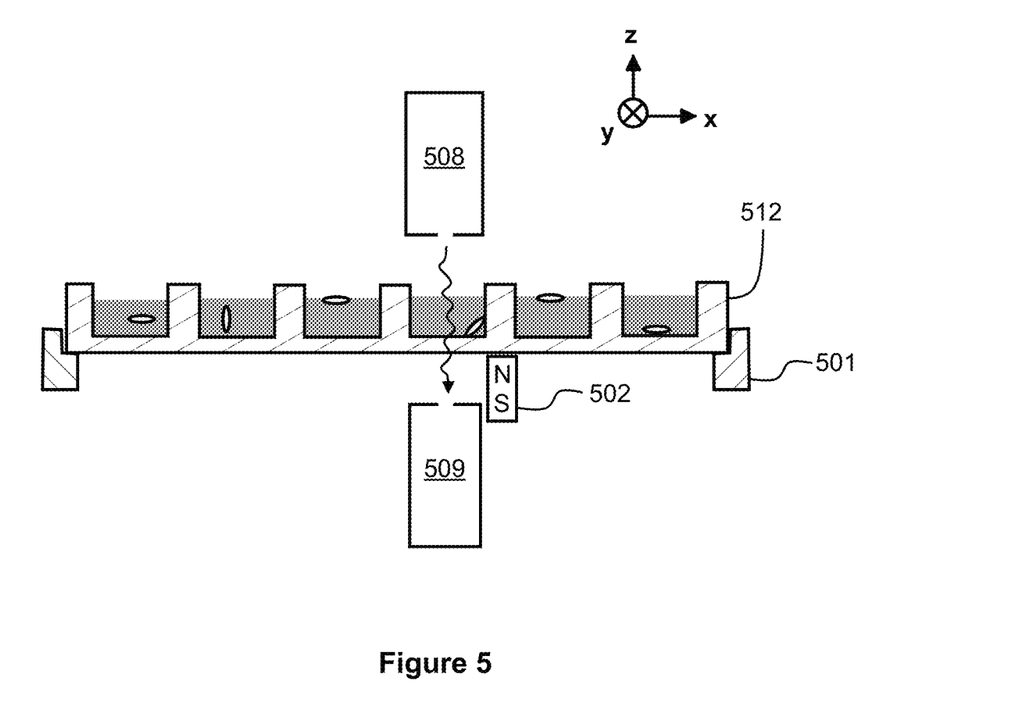
FIG. 5 shows a schematic side view of a device according to an exemplifying embodiment of the invention.

FIG. 5 shows a schematic side view of a device according to an exemplifying embodiment of the invention. In this exemplifying case, the device is an optical measurement instrument. The device comprises a support element 501 for supporting a sample well element 512, e.g. a microtitration plate, comprising sample wells. In FIG. 5, the sample well element 512 is presented as a section view. In the situation shown in FIG. 5, each sample well contains a piece that has been cut off from a solid sample carrier and that has been impregnated with sample material to be analyzed. Furthermore, the piece contains magnetically amplifying material. In addition to the piece, each sample well contains liquid which has dissolved the sample material or certain components of the sample material from the piece. The device further comprises a light source 508 for directing light to the liquid contained by a sample well and a detector 509 for measuring light generated by the light source and penetrated the liquid contained by the sample well. The sample well element 512 is assumed to be made of material that is sufficiently transparent for the light generated by the light source 508. The device comprises magnetizing equipment 502 arranged to produce magnetic field on the vicinity of a side wall of the sample well so that the magnetic field is capable of drawing the piece to the side wall of the sample well when the light penetrating the liquid contained by the sample well is measured. Thus, it can be ensured that the piece does not disturb the optical measurement.

Figure 6:
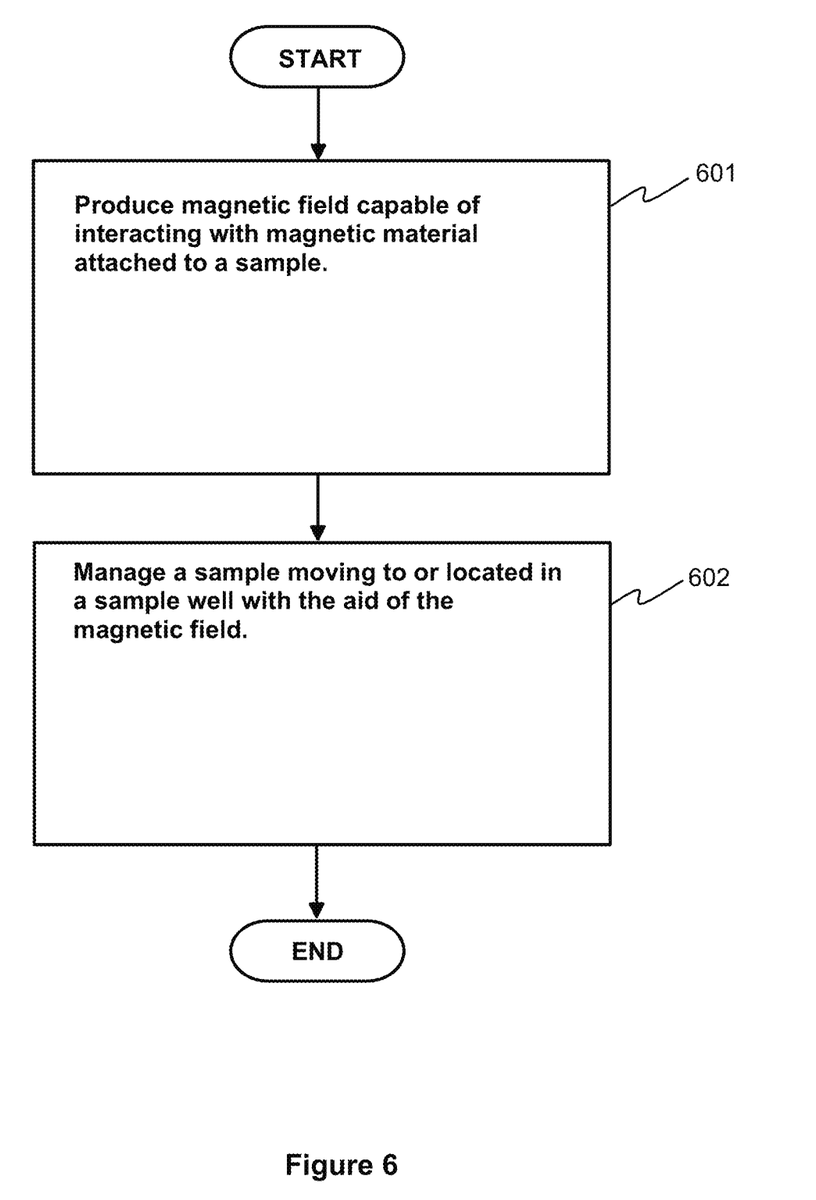
FIG. 6 shows a flow chart of a method according to an exemplifying embodiment of the invention for managing a sample to be analyzed.

FIG. 6 shows a flow chart of a method according to an exemplifying embodiment of the invention for managing a sample to be analyzed. The method comprises the following actions:

action 601: producing magnetic field capable of interacting with magnetically amplifying material attached to the sample, the magnetically amplifying material having relative magnetic permeability constant greater than one, and action 602: managing the sample with the aid of the magnetic field when the sample is moving to or located in a sample well.

A method according to an exemplifying embodiment of the invention comprises dispensing the sample, and subsequently, the sample is conveyed to the sample well. The magnetic field is directed to a route of the sample to the sample well, and a change caused in the magnetic field by the magnetically amplifying material attached to the sample moving to the sample well is detected so as to monitor whether the sample is correctly moved to the sample well.

In a method according to an exemplifying embodiment of the invention, the dispensing the sample comprises pipetting liquid sample carrier which is a colloid with dispersed phase particles comprising magnetically amplifying material. In this case, the dispensed quantity of the liquid sample carrier contains the sample to be analyzed. The above-mentioned particles can be, for example, poly-vinyl-alcohol "PVA" particles containing magnetite.

In a method according to an exemplifying embodiment of the invention, the dispensing the sample comprises cutting off a piece from a solid sample carrier containing magnetically amplifying material. In this case the piece carries the sample to be analyzed.

A method according to an exemplifying embodiment of the invention comprises adding liquid to the sample well and producing magnetic field on the vicinity of the bottom of the sample well so that the magnetic field draws a piece detached from a solid sample carrier containing magnetically amplifying material to the bottom of the sample well when the liquid is added to the sample well.

A method according to an exemplifying embodiment of the invention comprises directing excitation light to liquid contained by the sample well, measuring light emitted by the liquid contained by the sample well, and producing magnetic field on the vicinity of the bottom of the sample well so that the magnetic field draws a piece detached from a solid sample carrier containing magnetically amplifying material to the bottom of the sample well when the light emitted by the liquid contained by the sample well is measured.

A method according to an exemplifying embodiment of the invention comprises directing light to liquid contained by the sample well, measuring light penetrated the liquid contained by the sample well, and producing magnetic field on the vicinity of a side wall of the sample well so that the magnetic field draws a piece detached from a solid sample carrier containing magnetically amplifying material to the side wall of the sample well when the light penetrating the liquid contained by the sample well is measured.

The specific examples provided in the description given above should not be construed as limiting. Therefore, the invention is not limited merely to the exemplifying embodiments described above.

What is claimed is:

1. A device for managing a sample to be analyzed, the device comprising:
   a dispensing element that dispenses the sample to a sample well;
   magnetizing equipment that produces a magnetic field capable of interacting, when the sample is moving to the sample well, with magnetically amplifying material attached to the sample, the magnetically amplifying material having relative magnetic permeability constant greater than one,
   the magnetizing equipment being configured to produce the magnetic field on a route of the sample from the dispensing element to the sample well; and
   a sensor that detects a change caused in the magnetic field by the magnetically amplifying material attached to the sample moving to the sample well so as to monitor whether the sample is correctly moved to the sample well.

2. The device according to claim 1, wherein the dispensing element comprises a pipette for dispensing liquid sample carrier which is a colloid with dispersed phase particles comprising the magnetically amplifying material, a dispensed quantity of the liquid sample carrier containing the sample to be analyzed.

3. The device according to claim 1, wherein the dispensing element comprises a cutting element that cuts off a piece from a solid sample carrier containing the magnetically amplifying material, the piece carrying the sample to be analyzed.

4. The device according to claim 3, wherein the cutting element comprises a punch and a die provided with a channel for the punch, the punch being arranged to cut off the piece with a stroke through the solid sample carrier.

5. The device according to claim 1, the device further comprising:
   a liquid dispenser that adds liquid to the sample well,
   wherein the magnetizing equipment is further configured to produce a magnetic field on the vicinity of the bottom of the sample well so that the magnetic field is capable of drawing a piece detached from a solid sample carrier containing the magnetically amplifying material to the bottom of the sample well when the liquid is added to the sample well.

6. The device according to claim 1, the device further comprising:
   a light source that directs excitation light to liquid contained by the sample well; and
   a detector that measures light emitted by the liquid contained by the sample well,
   wherein the magnetizing equipment produces a magnetic field on the vicinity of the bottom of the sample well so that the magnetic field is capable of drawing a piece detached from a solid sample carrier containing the magnetically amplifying material to the bottom of the sample well when the light emitted by the liquid contained by the sample well is measured.

7. A method for managing a sample to be analyzed, the method comprising:
   dispensing the sample and moving the sample to a sample well;
   producing a magnetic field capable of interacting with magnetically amplifying material attached to the sample;
   managing the sample with the aid of the magnetic field when the sample is moving to the sample well, the magnetically amplifying material having a relative magnetic permeability constant greater than one, and the magnetic field being directed to a route of the sample to the sample well; and
   detecting a change caused in the magnetic field by the magnetically amplifying material attached to the sample moving to the sample well so as to monitor whether the sample is correctly moved to the sample well.

8. The method according to claim 7, wherein the dispensing the sample comprises pipetting liquid sample carrier, which is a colloid with dispersed phase particles comprising the magnetically amplifying material, a dispensed quantity of the liquid sample carrier containing the sample to be analyzed.

9. The method according to claim 8, wherein the particles are poly-vinyl-alcohol particles containing magnetite.

10. The method according to claim 7, wherein the dispensing the sample comprises cutting off a piece from a solid sample carrier containing the magnetically amplifying material, the piece carrying the sample to be analyzed.

11. The method according to claim 7, the method further comprising:
   adding liquid to the sample well and producing magnetic field on the vicinity of the bottom of the sample well so that the magnetic field draws a piece detached from a solid sample carrier containing the magnetically amplifying material to the bottom of the sample well when the liquid is added to the sample well.

12. The method according to claim 7, the method further comprising:
   directing excitation light to liquid contained by the sample well;
   measuring light emitted by the liquid contained by the sample well; and
   producing magnetic field on the vicinity of the bottom of the sample well so that the magnetic field draws a piece detached from a solid sample carrier containing the magnetically amplifying material to the bottom of the sample well when the light emitted by the liquid contained by the sample well is measured.

* * * * *